United States Patent [19]
Wu

[11] Patent Number: 5,254,794
[45] Date of Patent: Oct. 19, 1993

[54] ISOMERIZATION CATALYSTS AND PREPARATION THEREOF

[75] Inventor: An-hsiang Wu, Bartlesville, Okla.

[73] Assignee: Phillips Petroleum Company, Bartlesville, Okla.

[21] Appl. No.: 935,757

[22] Filed: Aug. 26, 1992

[51] Int. Cl.$^5$ .............................................. C07C 5/13
[52] U.S. Cl. ................................. 585/741; 585/734; 585/746; 585/747; 585/748
[58] Field of Search ............... 585/741, 746, 734, 747, 585/748

[56] References Cited

U.S. PATENT DOCUMENTS

| | | | |
|---|---|---|---|
| 2,820,074 | 1/1958 | Pines | 260/683.49 |
| 3,238,272 | 3/1966 | Nixon | 260/683.65 |
| 3,248,343 | 4/1966 | Kelly et al. | 252/442 |
| 3,420,909 | 1/1969 | Schmerling | 260/671 |
| 3,502,735 | 3/1970 | Copelin | 260/658 |
| 3,631,211 | 12/1971 | Schmerling | 260/668 C |
| 3,655,797 | 4/1972 | Schmerling | 260/671 |
| 3,846,503 | 11/1974 | Schmerling et al. | 260/666 P |
| 5,004,859 | 4/1991 | Schmidt et al. | 585/741 |

OTHER PUBLICATIONS

N. Kitajima, "Two Component Friedel-Crafts Catalysts", Materials Chemistry and Physics 17(1987), pp. 31–48.

N. Kitajima et al., "Cu(AlCl$_4$)$_2$ as a Catalyst for the Isomerization of Pentane at Room Temperature", Journal of Molecular Catalysis 10 (1981), pp. 121–122.

Y. Ono et al., "Isomerization of Pentane with AlCl$_3$—CuSO$_4$ Mixtures", Journal of Catalysis 64 (1980), pp. 13–17.

Y. Ono et al., "Isomerization of Pentane with Aluminum Chloride (Gallium Chloride)-Cupric Salt Complexes", Proceedings 7th Internat. Congress Catalys., Tokyo, 1980, pp. 1006–1017.

Primary Examiner—Asok Pal
Assistant Examiner—P. Achutamurthy
Attorney, Agent, or Firm—K. K. Brandes

[57] ABSTRACT

Isomerization catalyst compositions are prepared by heating aluminum chloride, at least one of several metal salts (preferably CuSO$_4$), at least one of several inorganic support materials (alumina, silica, aluminum phosphate and combinations thereof) and at least one chlorinated hydrocarbon (preferably CCl$_4$) at a temperature of about 40°–90° C. The dried catalyst compositions are used for the isomerization of C$_5$–C$_{10}$ cycloalkanes and/or C$_4$–C$_{10}$ alkanes.

23 Claims, No Drawings

ISOMERIZATION CATALYSTS AND PREPARATION THEREOF

BACKGROUND OF THE INVENTION

In one aspect, this invention relates to the isomerization of alkanes and/or cycloalkanes. In another aspect, this invention relates to the preparation of materials which are effective catalysts for isomerizing alkanes and/or cycloalkanes.

The use of combinations of aluminum halide (in particular AlCl$_3$) and certain metal chlorides and sulfates (in particular CuCl$_2$ or CuSO$_4$) for alkane isomerization is known and has been described in various scientific articles. The present invention is directed to modifying these catalysts and, thus, improving their catalytic activity and/or selectivity.

SUMMARY OF THE INVENTION

It is an object of this invention to prepare catalyst materials from aluminum chloride, various metal salts and support materials. It is another object of this invention to employ these catalyst materials for isomerizing alkanes. It is a further object of this invention to employ these materials for isomerizing cycloalkanes. Other objects and advantages will be apparent from the detailed description of the invention and the appended claims.

In accordance with this invention, a method of preparing compositions of matter (effective as alkane and/or cycloalkane isomerization catalyst compositions) comprises the steps of:

(1) heating for a period of at least 1 hour, at a temperature in the range of about 40° C. to about 90° C., in the substantial absence of water: a mixture comprising (a) aluminum chloride, (b) at least one metal salt selected from the group consisting of copper(II) chloride, copper(II) sulfate, iron(II) sulfate, cobalt(II) sulfate, nickel(II) sulfate, manganese(II) sulfate, zinc sulfate, magnesium sulfate and calcium sulfate, (c) at least one solid inorganic refractory material having a BET/N$_2$ surface area of at least 50 m$^2$/g selected from the group consisting of alumina, silica, silica-alumina, aluminum phosphate and aluminum phosphate/oxide and (d) at least one chlorinated hydrocarbon having a normal boiling point (i.e., at a pressure of about 1 atm.) of about 40°-90° C.; wherein the molar ratio of aluminum chloride to said at least one metal salt is at least about 2:1; and (2) separating the solid material contained in the reaction mixture formed in step (1) from said at least one chlorinated hydrocarbon under a dry gas atmosphere.

The preferred agent (b) is CuSO$_4$. The preferred agent (d) is carbon tetrachloride. Preferably, the heating time in preparation step (1) is about 5-30 hours. In a further preferred embodiment, step (2) is carried out in two substeps: filtering the reaction mixture formed in step (1) so as to recover the solid component therefrom, and subsequently drying the recovered solid material (i.e., substantially removing volatile substances, in particular the at least one chlorinated hydrocarbon, therefrom).

Also in accordance with this invention, a cycloalkane conversion process comprises contacting, at a temperature of up to about 100° C. (preferably about 20°-50° C.), at least one cycloalkane containing 5-10 carbon atoms per molecule with at least one of the isomerization catalyst compositions having been prepared by the above-outlined preparation method comprising steps (1) and (2), at such contacting conditions as to at least partially convert said at least one feed cycloalkane to at least one product cycloalkane isomer (having the same number of C atoms per molecule as said at least one feed cycloalkane but having a different structural formula). Preferably, the feed cycloalkane is a methyl-substituted cycloalkane. More preferably, the feed cycloalkane is methylcyclopentane which is at least partially isomerized to cyclohexane.

Further in accordance with this invention, an alkane conversion process comprises the step of contacting, at a temperature of up to about 100° C. (preferably about 20°-50° C.), at least one feed alkane (i.e., at least one normal alkane or at least one isoalkane or a mixture thereof) containing about 4-10 carbon atoms per molecule with at least one of the isomerization catalyst compositions having been prepared by the above-outlined preparation method comprising steps (1) and (2), at such contacting conditions as to convert a portion of said at least one feed alkane to at least one product alkane isomer (having the same number of C atoms per molecule as said at least one feed alkane but having a different structural formula).

Concurrently with the isomerization of a portion of feed alkane(s), another portion of feed alkane(s) is generally disproportionated, i.e., converted to a mixture of at least one alkane having a higher number of carbon atoms per molecule and at least one alkane having a lower number of carbon atoms per molecule than the feed alkane(s). Preferred feed alkanes are normal (straight chain) C$_5$-C$_8$ alkanes and branched C$_5$-C$_8$ alkanes (isoalkanes).

DETAILED DESCRIPTION OF THE INVENTION

Step (a) of the preparation process of this invention can be carried out in any suitable manner in any suitable vessel. Generally, substantially dry agents (a), (b), (c) and (d), which are defined above, are thoroughly mixed under a dry inert gas atmosphere (N$_2$, He, Ar and the like), and then heated under a dry inert gas atmosphere at a temperature of about 40°-90° C., preferably about 70°-80° C., for a time period of about 4 to about 120 hours, preferably about 10-30 hours, more preferably 15-25 hours. It is preferred to carry out step (a) with agitation, either mechanically (e.g., by means of a stirrer) or ultrasonically.

The molar ratio of agent (a), i.e., AlCl$_3$, to agent (b), preferably CuSO$_4$, should be at least about 2:1, preferably is about 2:1 to about 10:1, and more preferably is about 5:1 to about 6:1. Generally, the ratio of the combined weight of agents (a) and (b) to the weight of agent (c), i.e., one of the solid inorganic refractory materials listed above, is in the range of about 0.5:1 to about 5:1, preferably about 1:1 to about 2:1. These inorganic refractory materials are either commercially available or can be prepared by known methods. The surface area of agent (c) should be at least about 50 m$^2$/g, and preferably is about 100-400 m$^2$/g, as determined by the well known method of Brunauer, Emmett and Teller (BET method) employing nitrogen. Preferred refractory support materials are those consisting essentially of alumina, silica, silica-aluminas having a silica:alumina weight ratio of about 0.2:1 to about 1.5:1 (more preferably about 0.25:1 to about 1:1; generally having been prepared by coprecipitation of hydrated silica and hydrated alumina, followed by drying and calcining), aluminum phosphates (generally having an atomic Al:P ratio of about 1:1 to about 2:1), and aluminum phosphate/oxides (having an atomic Al:P ratio of about 0.6:1. to about 10:1; generally having been prepared by coprecipitation of aluminum phosphate and hydrated alumina, followed by drying and calcining). It is within the scope of this invention to use refractory support materials (in particular $Al_2O_3$, $SiO_2$ and $SiO_2$—$Al_2O_3$) which have been pretreated with a dilute aqueous $H_2SO_4$ solution (about 0.05–0.2 normal), followed by drying and calcining (as described in Example XII).

Agent (d) is a chlorinated hydrocarbon or a mixture of two or more chlorinated hydrocarbons having a normal boiling point in the range of about 40°–90° C., preferably about 70°–80° C. Non-limiting examples of agent (d) include dichloromethane, chloroform (trichloromethane), carbon tetrachloride, 1,1-dichloroethane, 1,2-dichloroethane, 1,1,1-trichloroethane, 1,1-dichloropropane, 2,2-dichloropropane, 1-chlorobutane, 2-chloro-2-methylbutane, and mixtures thereof. The preferred agent (d) is carbon tetrachloride. Generally the ratio of the weight of agent (d) to the combined weight of agents (a), (b) and (c) is about 4:1 to about 20:1.

Separation step (2) can be carried out in any suitable manner. Preferably, the finished reaction mixture of step (1) is filtered, and the solid filter cake is substantially dried at any suitable conditions, preferably at subatmospheric (i.e., vacuum) conditions, at a temperature of about 25°–60° C. Preferably, step (2) is carried out under a dry inert gas atmosphere ($N_2$, He, Ar, and the like). The finished/dried catalyst particles should be stored under a dry inert gas atmosphere.

Also in accordance with this invention, the catalyst composition described above is employed for isomerizing $C_5$–$C_{10}$ cycloalkanes, preferably methyl-substituted cycloalkanes. Nonlimiting examples of suitable feed cycloalkanes are methylcyclobutane, methylcyclopentane, 1,1-dimethylcyclopentane, 1,2-dimethylcyclopentane, 1,3-dimethyleyclopentane, methylcyclohexane, 1,1-dimethylcyclohexane, 1,2-dimetbylcyclohexane, 1,3-dimethylcyclohexane, ethylcyclohexane, methylcycloheptane, 1,methyl-2-ethyleyclopentane, 1,1-dimethylcycloheptane, 1,2-dimethylcycloheptane, 1,3-dimethylcycloheptane, ethylcyclobeptane, 1-methyl-2-ethyleyclohexane, methylcyclooetane, 1,1-dimethylcyclooctane, 1,2-dimethylcyclooctane, 1,3-dimethylcyclooctane, and mixtures thereof. The preferred cycloalkane is methylcyclopentane which is substantially converted to cyclohexane in accordance with the process of this invention.

Further, in accordance with this invention, the catalyst composition described above is employed for partially isomerizing (and partially disproportionating) normal (straight chain) alkanes and isoalkanes (i. e., branched) alkanes containing 4–10 carbon atoms per molecule. Non-limiting examples of suitable alkanes are n-butane, isobutane, n-pentane, isopentane (i.e., 2-methylbutane), n-hexane, isohexanes (such as 2-methylpentane, 3-methyl-pentane, 2.2-dimethylbutane), n-heptane, isoheptanes (in particular methyl-substituted hexanes and dimethyl-substituted pentanes), n-octane, isooctanes (in particular methyl-substituted heptanes and dimethyl-substituted hexanes), n-nonane, isononanes (in particular methyl-substituted octanes, dimethyl-substituted heptanes, trimethyl-substituted hexanes), n-decane and isodecanes (in particular methyl-substituted nonanes, dimethyl-substituted octanes, trimethyl-substituted heptanes, tetramethyl-substituted hexanes). Presently preferred are $C_4$–$C_8$ n-alkanes and $C_4$–$C_8$ isoalkanes, such as those present in commercial alkylation products (i.e., products obtained by the reaction of an isoalkane such as isobutane with an alkene such as butene-2). Particularly preferred feed alkanes are n-pentane, n-hexane, isopentane (2-methylbutane), and 2,2,4-trimethylpentane.

The process for isomerizing $C_4$–$C_{10}$ alkanes or $C_5$–$C_{10}$ cycloalkanes or mixtures of alkanes and cycloalkanes (at any suitable weight ratio) with one of the above-described catalyst compositions can be carried out under any suitable reaction conditions at a relatively low temperature of up to about 100° C., more preferably about 20°–50° C.; most preferably about 30°–40° C., generally at about 1–5 atm. pressure. The feed alkane(s) and/or cycloalkane(s) can be contacted with the catalyst composition in any suitable mode, such as in a slurry-type operation in which the catalyst is dispersed in the feed hydrocarbon(s), or in a fixed catalyst bed operation in which the hydrocarbon feed flows upward or downward through a solid catalyst layer (or several catalyst layers). The time of contact between the feed alkane(s) and/or cycloalkane(s) and the catalyst composition generally is in the range of about 5 minutes to about 8 hours, preferably about 1–2 hours. The isomerization process can be carried out as a batch operation or as a continuous operation. Moisture is to be substantially absent during the isomerization process.

The isomerization processes of this invention frequently generate a multitude of products, especially in the case of alkanes which do not only partially isomerize but also, to a lesser or greater extent, disproportionate to higher and lower alkanes. Thus, it is generally necessary to separate the various formed hydrocarbon products from one another and from unconverted feed hydrocarbons. This separation can be carried out in any suitable manner, generally by fractional distillation (possibly in the presence of an extractant, i.e., by extractive distillation) as is easily determined by persons skilled in the various liquid-liquid separation technologies.

The following examples are provided to further illustrate the processes of this invention, and are not to be construed as unduly limiting the scope of this invention.

EXAMPLE I

This example illustrates the effect of the surface area of alumina used in the preparation of $AlCl_3/CuSO_4/Al_2O_3$ catalysts on their isomerization activity.

Catalyst A (Control) was prepared as follows: 1.78 grams (13.3 millimole) of $AlCl_3$, 0.80 grams (5.0 millimole) of $CuSO_4$, 10.0 grams of Alundum ® (calcined alpha-alumina having a surface area of about 1.0 m²/g, marketed by Norton Company, Worcester, Mass.) and about 40 mL of $CCl_4$ were mixed and heated for 18 hours under reflux conditions in a dry nitrogen gas atmosphere. Thereafter, the slurry was cooled and filtered, and the solid catalyst material was dried under vacuum conditions.

Catalyst B (Invention) was prepared essentially in accordance with the procedure for Catalyst A, except that 5.0 g of a gamma-alumina (100 mesh trilobal extrudate; marketed by American Cyanamid Company, Deerfield, Ill.; having a BET/$N_2$ surface area of 180 m²/g and a pore volume of 1.02 cc/g) was used in lieu of Alundum ®.

Catalysts A and B were tested for their isomerization activity as follows: 1.0 gram of each catalyst and 20 mL of dry n-pentane (freshly distilled from sodium metal and benzophenone) were placed in a sealed glass flask and kept at room temperature (about 22° C.) and atmospheric pressure (1 atm.) with slight agitation. After about 1 hour, the flask content was analyzed by means of a gas chromatograph. Test results are summarized in Table I.

TABLE I

| Catalyst | Product Composition (Mol-%) | | | | %-Conversion of n-Pentane |
|---|---|---|---|---|---|
| | n-Pentane | Isopentane | $C_1$–$C_4$ Alkanes | $C_6^+$ Alkanes | |
| A (Control) | 98.67 | 0.78 | 0.10 | 0.45 | 1.3 |
| B (Invention) | 81.98 | 12.26 | 2.30 | 3.46 | 18.0 |

Test results in Table I clearly demonstrate that Catalyst A which was prepared from a low surface area alumina was much less active as an alkane isomerization catalyst than Catalyst B which was prepared from a high surface area alumina. Based on these results, it is concluded that the support material in the catalyst compositions of this invention should have a BET/$N_2$ surface area of at least about 50 $M^2/g$.

EXAMPLE II

This example illustrates the effect of the atomic Al:Cu ratio in $ACl_3/CuSO_4/Al_2O_3$ catalysts on their alkane isomerization activity.

Catalyst C (Control) was prepared as follows: 1.33 grams (10 millimoles) of $AlCl_3$, 1.59 grams (10 millimoles) of $CuSO_4$, 5.0 grams of gamma-alumina (trilobal extrudate having a BET/$N_2$ surface area of about 144 $m^2/g$; having been calcined in air for 2–3 hours at 700° C.) and 30 mL of dried carbon tetrachloride were mixed and heated for 1 day under reflux conditions in a nitrogen gas atmosphere. Thereafter, the obtained slurry was cooled and filtered, and the yellow solid was dried under vacuum conditions. The atomic ratio of Al:Cu in Catalyst C was 1:1.

Catalyst D (Control) was prepared essentially in accordance with the procedure for Catalyst C, except that 2.67 grams (20 millimoles) $AlCl_3$, 3.80 grams (24 millimoles) $CuSO_4$, 10.0 grams of $Al_2O_3$ and 60 mL of $CCl_4$ were used, and the mixture was heated for 3 days in a nitrogen atmosphere under reflux conditions. The atomic ratio of Al:Cu in Catalyst D was about 0.8:1.

Catalyst E (Invention) was prepared as follows: 2.67 grams (20 millimoles) of $AlCl_3$, 1.66 grams (10 millimoles) of $CuSO_4$, 5.0 grams of calcined gamma-alumina, and 60 mL of dried carbon tetrachloride were heated for 5 days in a dry nitrogen gas atmosphere under reflux conditions. The reaction mixture was cooled and filtered, and the obtained solid material was dried under vacuum conditions. The atomic ratio of Al:Cu in Catalyst E was 2:1.

Catalyst F (Invention) was prepared essentially in accordance with the procedure for Catalyst E, except that 3.56 grams (27 millimoles) of $AlCl_3$, 1.59 grams (10 millimoles) of $CuSO_4$, 10.0 grams of calcined $Al_2O_3$ and 60 mL of dried $CCl_4$ were used, and the heating time (in $N_2$ and under reflux conditions) was about 2 days. The atomic ratio of Al:Cu in Catalyst F was 2.7:1.

Catalysts C, D, E and F were tested for n-pentane isomerization activity, essentially in accordance with the procedure described in Example I. Test results (after a reaction time of 3 hours) are summarized in Table II.

TABLE II

| Catalyst | Product Composition (Mol-%) | | | | % Conversion of n-Pentane |
|---|---|---|---|---|---|
| | n-Pentane | Isopentane | $C_1$–$C_4$ Alkanes | $C_6^+$ Alkanes | |
| C (Control) | 100 | 0 | 0 | 0 | 0 |
| D (Control) | 100 | 0 | 0 | 0 | 0 |
| E (Invention) | 60.58 | 26.36 | 2.56 | 10.50 | 39.4 |
| F (Invention) | 38.14 | 20.87 | 5.96 | 34.33 | 61.9 |

Test results in Table II clearly show that Catalysts C and D having an atomic Al:Cu ratio of about 1:1 were essentially inactive as n-pentane isomerization catalysts, whereas invention Catalysts E and F having an atomic Al:Cu ratio of about 2:1 and higher were quite effective as n-pentane isomerization catalysts. Test data in Table II also indicate that in the presence of Catalysts E and F, a substantial portion of n-pentane was disproportionated to $C_1$–$C_4$ and $C_6$ alkanes (the latter being desirable gasoline blending components).

EXAMPLE III

In this example, the use of $CuSO_4$ in the preparation of isomerization catalysts is compared with the use of $CuCl_2$.

Catalyst G was prepared essentially in accordance with the procedure for Catalyst E, except that 1.36 grams (10 millimoles) of $CuCl_2$ were used in lieu of $CuSO_4$. The atomic ratio of Al:Cu in Catalyst G was 2:1.

Catalyst H was prepared essentially in accordance with the procedure for Catalyst F, except that 1.78 grams (13 millimoles) of $CuCl_2$ were used in lieu of $CuSO_4$. The atomic ratio of Al:Cu was 2:1.

Catalyst E (described in Example II) and Catalyst G, were tested for their activity to catalyze the conversion of methylcyclopentane to cyclohexane at room temperature, essentially in accordance with the procedure described in Example I, except that 20 mL of methylcyclopentane (MCP) was used as the hydrocarbon feed. Test results after 2 hours are listed in Table III.

TABLE III

| Catalyst | % Conversion of Methylcyclopentane | % Selectivity[1] to Cyclohexane |
|---|---|---|
| G | 12.3 | 92 |
| E | 31.8 | 98 |

[1]mole percentage of cyclohexane in product divided by %-conversion of methylcyclopentane, multiplied by 100.

Test results in Table II indicate that Catalyst E (i.e. the catalyst material prepared from $CuSO_4$) was more active as a cycloalkane isomerization catalyst than Catalyst G (i.e., the corresponding material prepared from $CuCl_2$). Thus, $CuSO_4$ is the preferred copper salt used in the preparation of the catalysts (to be employed for alkane and/or cycloalkane isomerization), in accordance with this invention. Furthermore, test data in Table III indicate that methylcyclopentane was almost completely isomerized to cyclohexane in the presence of Catalyst E. Essentially no disproportionation of methylcyclohexane to higher and lower hydrocarbons was detected.

Catalyst F (described in Example II) and Catalyst H were tested at room temperature as n-pentane isomerization catalysts, essentially in accordance with the procedure described in Example I. Test results after 2 hours are summarized in Table IV.

TABLE IV

| Catalyst | Product Composition (Mol-%) | | | | % Conversion of n-Pentane |
|---|---|---|---|---|---|
| | n-Pentane | Isopentane | $C_1$-$C_4$ Alkane | $C_6^+$ Alkanes | |
| H | 93.64 | 4.47 | 0.93 | 0.96 | 6.4 |
| F | 66.47 | 23.41 | 5.19 | 4.93 | 33.5 |

Test data in Table IV show that the catalyst material prepared from $CuSO_4$ (Catalyst F) was a more active alkane isomerization catalyst than the corresponding catalyst material prepared from $CuCl_2$ (Catalyst H). Preliminary test data (not described in detail herein) indicate that materials prepared from $AlBr_3$, $CuSO_4$ and alumina by refluxing in $CCl_4$, as described above, were also active as n-pentane isomerization catalysts, but were less effective than the corresponding catalyst materials prepared from $AlCl_3$, $CuSO_4$ and alumina in accordance with the preparation method of this invention.

EXAMPLE V

This example illustrates the preparation of numerous catalyst compositions, substantially in accordance with the preparation of Catalysts E and F, except that metal sulfates other than $CuSO_4$ and support materials other than alumina were also used. The molar ratio of $AlCl_3$ to the metal sulfates was generally about 5.3:1. The metal sulfates (all essentially anhydrous) which were employed in conjunction with $AlCl_3$ were: $CuSO_4$, $NiSO_4$, $CoSO_4$, $FeSO_4$, $MnSO_4$, $ZnSO_4$, $MgSO_4$ and $CaSO_4$.

The following 100 mesh support materials were generally employed in the preparation of these catalysts: alumina (described in Example II), silica (calcined at about 600° C. for about 3 hours; surface area: 340 $m^2/g$; marketed by the Davison Catalyst Division of W. R. Grace and Company, Baltimore, Md., under the product designation of G-57); a silica-alumina containing 50 weight-% of each component and a silica-alumina containing 25 weight-% silica and 75 weight-% alumina (both having also been prepared by coprecipitating hydrated silica and hydrated alumina, followed by calcining at about 600° C. for about 2 hours; surface area: about 300–330 $m^2/g$); and various coprecipitated aluminum phosphate/oxide materials wherein the atomic Al:P ratios were in the range of from 0.2:1 to 0.9:1, having been prepared by adding enough of a concentrated aqueous ammonia solution to an aqueous solution containing $Al(NO_3)_3$ and $NH_4H_2PO_4$ (at the desired Al:P ratio) to make the latter solution basic and to coprecipitate aluminum phosphate/hydroxide, followed by aging the coprecipitated aluminum phosphate/hydroxide under the basic solution for 1–2 hours, filtering the aqueous slurry, drying and calcining the filter cake in air for about 3 hours at 600° C.

EXAMPLE VI

This example illustrates the use of the catalyst materials described in Example V for n-pentane isomerization/disproportionation, essentially in accordance with the procedure described in Example I, except that generally the reaction temperature was about 30°–40° C. Test results obtained after a reaction time of about 1 hour are summarized in Table V.

TABLE V

| Catalyst Preparation Method | Liquid Product Composition (Weight-%) | | | | % Conversion of n-Pentane |
|---|---|---|---|---|---|
| | n-Pentane | Isopentane | $C_4$ Alkanes | $C_6^+$ Alkanes | |
| $AlCl_3$ + $CuSO_4$ + $Al_2O_3$ | 49.8 | 25.6 | 7.1 | 17.6 | 50.2 |
| $AlCl_3$ + $CuSO_4$ + $Al_2O_3$ | 52.9 | 29.4 | 7.7 | 10.1 | 47.1 |
| $AlCl_3$ + $CuSO_4$ + $SiO_2$ | 43.7 | 24.8 | 11.7 | 19.8 | 56.3 |
| $AlCl_3$ + $CuSO_4$ + $SiO_2/Al_2O_3^1$ | 33.2 | 32.8 | 18.3 | 15.7 | 66.8 |
| $AlCl_3$ + $CuSO_4$ + $SiO_2/Al_2O_3^2$ | 45.7 | 29.9 | 9.0 | 15.4 | 54.3 |
| $AlCl_3$ + $CuSO_4$ + $SiO_2/Al_2O_3^2$ | 35.0 | 31.3 | 10.0 | 23.8 | 65.0 |
| $AlCl_3$ + $CuSO_4$ + Al—$PO_4^3$ | 62.3 | 26.9 | 5.1 | 5.7 | 37.7 |
| $AlCl_3$ + $CuSO_4$ + Al—$PO_4^4$ | 35.8 | 29.1 | 19.1 | 16.0 | 64.2 |
| $AlCl_3$ + $CuSO_4$ + Al—$PO_4^5$ | 33.9 | 30.9 | 20.1 | 15.1 | 66.1 |
| $AlCl_3$ + $CuSO_4$ + Al—$PO_4^5$ | 31.7 | 30.8 | 15.8 | 21.7 | 68.3 |
| $AlCl_3$ + $CuSO_4$ + Al—$PO_4^6$ | 26.9 | 30.1 | 17.2 | 25.9 | 73.1 |
| $AlCl_3$ + $CuSO_4$ + Al—$PO_4^7$ | 25.2 | 30.0 | 25.1 | 19.7 | 74.8 |
| $AlCl_3$ + $CuSO_4$ + Al—$PO_4^8$ | 42.1 | 32.6 | 13.1 | 12.3 | 67.9 |
| $AlCl_3$ + $NiSO_4$ + $Al_2O_3$ | 87.0 | 10.5 | 1.0 | 1.5 | 13.0 |
| $AlCl_3$ + $NiSO_4$ + $SiO_2$ | 71.5 | 16.2 | 5.4 | 7.0 | 28.5 |
| $AlCl_3$ + $NiSO_4$ + $SiO_2/Al_2O_3^1$ | 78.4 | 18.4 | 0.8 | 2.4 | 21.6 |
| $AlCl_3$ + $NiSO_4$ + $SiO_2/Al_2O_3^2$ | 70.5 | 16.0 | 6.3 | 7.2 | 29.5 |
| $AlCl_3$ + $NiSO_4$ + Al—$PO_4^6$ | 68.5 | 21.7 | 2.7 | 7.1 | 31.5 |
| $AlCl_3$ + $CoSO_4$ + $Al_2O_3$ | 54.3 | 23.0 | 5.9 | 16.9 | 45.7 |

TABLE V-continued

| Catalyst Preparation Method | Liquid Product Composition (Weight-%) | | | | % Conversion of n-Pentane |
|---|---|---|---|---|---|
| | n-Pentane | Isopentane | $C_4$ Alkanes | $C_6^+$ Alkanes | |
| $AlCl_3$ + $CoSO_4$ + $SiO_2$ | 46.5 | 24.1 | 11.5 | 18.0 | 53.5 |
| $AlCl_3$ + $CoSO_4$ + $SiO_2/Al_2O_3$[1] | 49.5 | 24.2 | 5.8 | 20.5 | 50.5 |
| $AlCl_3$ + $CoSO_4$ + $SiO_2/Al_2O_3$[2] | 64.5 | 19.0 | 6.4 | 10.1 | 35.5 |
| $AlCl_3$ + $CoSO_4$ + Al—$PO_4$[6] | 45.2 | 28.0 | 13.1 | 13.7 | 54.8 |
| $AlCl_3$ + $FeSO_4$ + $Al_2O_3$ | 85.9 | 9.4 | 2.2 | 2.5 | 14.1 |
| $AlCl_3$ + $FeSO_4$ + $SiO_2$ | 63.8 | 18.0 | 9.3 | 8.9 | 36.2 |
| $AlCl_3$ + $FeSO_4$ + $SiO_2/Al_2O_3$[1] | 51.5 | 26.0 | 6.9 | 15.6 | 48.5 |
| $AlCl_3$ + $FeSO_4$ + $SiO_2/Al_2O_3$[2] | 62.2 | 19.6 | 6.4 | 11.9 | 37.8 |
| $AlCl_3$ + $FeSO_4$ + Al—$PO_4$[6] | 54.3 | 29.1 | 5.7 | 10.9 | 45.7 |
| $AlCl_3$ + $MnSO_4$ + $Al_2O_3$ | 84.4 | 11.1 | 2.0 | 2.5 | 15.6 |
| $AlCl_3$ + $MnSO_4$ + $SiO_2$ | 61.9 | 23.6 | 5.4 | 9.1 | 38.1 |
| $AlCl_3$ + $MnSO_4$ + $SiO_2/Al_2O_3$[1] | 84.5 | 10.9 | 1.7 | 2.9 | 15.5 |
| $AlCl_3$ + $MnSO_4$ + $SiO_2/Al_2O_3$[2] | 61.8 | 21.6 | 6.4 | 10.3 | 38.2 |
| $AlCl_3$ + $MnSO_4$ + Al—$PO_4$[6] | 68.1 | 21.5 | 3.8 | 6.6 | 31.9 |
| $AlCl_3$ + $ZnSO_4$ + $Al_2O_3$ | 81.2 | 13.8 | 2.4 | 2.7 | 18.4 |
| $AlCl_3$ + $ZnSO_4$ + $SiO_2$ | 48.3 | 24.9 | 7.9 | 18.9 | 51.7 |
| $AlCl_3$ + $ZnSO_4$ + $SiO_2/Al_2O_3$[1] | 80.6 | 11.4 | 3.5 | 4.5 | 19.4 |
| $AlCl_3$ + $ZnSO_4$ + $SiO_2/Al_2O_3$[2] | 63.0 | 21.3 | 6.6 | 9.1 | 37.0 |
| $AlCl_3$ + $ZnSO_4$ + Al—$PO_4$[6] | 68.3 | 22.6 | 3.3 | 5.9 | 31.7 |
| $AlCl_3$ + $MgSO_4$ + $Al_2O_3$ | 84.2 | 11.1 | 2.2 | 2.5 | 15.8 |
| $AlCl_3$ + $MgSO_4$ + $SiO_2$ | 54.8 | 22.0 | 7.6 | 15.7 | 45.2 |
| $AlCl_3$ + $MgSO_4$ + $SiO_2/Al_2O_3$[1] | 73.4 | 19.7 | 2.7 | 4.1 | 26.6 |
| $AlCl_3$ + $MgSO_4$ + $SiO_2/Al_2O_3$[2] | 51.3 | 27.7 | 7.6 | 13.5 | 48.7 |
| $AlCl_3$ + $MgSO_4$ + Al—$PO_4$[6] | 64.5 | 27.7 | 2.1 | 5.7 | 35.5 |
| $AlCl_3$ + $CaSO_4$ + $Al_2O_3$ | 92.0 | 5.1 | 1.3 | 1.6 | 8.0 |
| $AlCl_3$ + $CaSO_4$ + $SiO_2$ | 88.4 | 6.0 | 2.1 | 3.5 | 11.6 |
| $AlCl_3$ + $CaSO_4$ + $SiO_2/Al_2O_3$[1] | 83.4 | 12.9 | 0.7 | 3.0 | 16.6 |
| $AlCl_3$ + $CaSO_4$ + $SiO_2/Al_2O_3$[2] | 82.9 | 9.6 | 3.3 | 4.1 | 17.1 |
| $AlCl_3$ + $CaSO_4$ + Al—$PO_4$[6] | 53.5 | 30.0 | 6.1 | 10.5 | 46.5 |

[1] 50 weight-% silica + 50 weight-% $Al_2O_3$
[2] 25 weight-% silica + 75 weight-% $AlO_3$
[3] aluminum phosphate/oxide having a P:Al atomic ratio of 0.2:1
[4] aluminum phosphate/oxide having a P:Al atomic ratio of 0.3:1
[5] aluminum phosphate/oxide having a P:Al atomic ratio of 0.4:1
[6] aluminum phosphate/oxide having a P:Al atomic ratio of 0.5:1
[7] aluminum phosphate/oxide having a P:Al atomic ratio of 0.6:1
[8] aluminum phosphate/oxide having a P:Al atomic ratio of 0.9:1

Test results in Table V indicate that generally the catalysts prepared from $AlCl_3$, $CuSO_4$ and either an aluminum phosphate/oxide having a P:Al atomic ratios of about 0.3–0.9:1 or a silica-alumina exhibited the highest activity.

EXAMPLE VII

This example illustrates the use of the catalyst materials described in Example V for n-hexane isomerization/disproportionation, essentially in accordance with the procedure described in Example I, except that generally the reaction temperature was about 30°–40° C. Test results obtained after a reaction time of about 1 hour (in some cases after about 2 hours) are summarized in Table VI.

TABLE VI

| Catalyst Preparation Method | Liquid Product Composition (Weight-%) | | | | % Conversion of n-Hexane |
|---|---|---|---|---|---|
| | n-Hexane | Isohexanes[9] | $C_4/C_5$ Alkanes | $C_7^+$ Alkanes | |
| $AlCl_3$ + $CuSO_4$ + $Al_2O_3$ | 82.3 | 9.9 | 4.5 | 3.2 | 17.7 |
| $AlCl_3$ + $CuSO_4$ + $Al_2O_3$ | 84.5 | 8.8 | 5.0 | 1.7 | 15.5 |
| $AlCl_3$ + $CuSO_4$ + $SiO_2$ | 83.8 | 7.9 | 4.9 | 3.5 | 16.2 |
| $AlCl_3$ + $CuSO_4$ + $SiO_2/Al_2O_3$[1] | 79.0 | 10.7 | 6.7 | 3.6 | 21.0 |
| $AlCl_3$ + $CuSO_4$ + $SiO_2/Al_2O_3$[2] | 79.5 | 10.6 | 6.1 | 3.9 | 20.5 |
| $AlCl_3$ + $CuSO_4$ + $SiO_2/Al_2O_3$[2] | 81.3 | 10.1 | 5.3 | 3.3 | 18.7 |
| $AlCl_3$ + $CuSO_4$ + $SiO_2/Al_2O_3$[2] | 79.4 | 10.1 | 7.0 | 3.4 | 20.6 |
| $AlCl_3$ + $CuSO_4$ + Al—$PO_4$[3] | 75.7 | 13.7 | 5.8 | 4.8 | 24.3 |
| $AlCl_3$ + $CuSO_4$ + Al—$PO_4$[4] | 67.8 | 14.1 | 9.9 | 8.2 | 32.2 |
| $AlCl_3$ + $CuSO_4$ + Al—$PO_4$[5] | 64.3 | 14.4 | 12.7 | 8.6 | 35.7 |
| $AlCl_3$ + $CuSO_4$ + Al—$PO_4$[5] | 76.0 | 11.5 | 8.1 | 4.4 | 24.0 |
| $AlCl_3$ + $CuSO_4$ + Al—$PO_4$[6] | 68.9 | 13.6 | 10.6 | 6.9 | 31.1 |
| $AlCl_3$ + $CuSO_4$ + Al—$PO_4$[7] | 73.6 | 12.7 | 9.1 | 4.7 | 26.4 |
| $AlCl_3$ + $CuSO_4$ + Al—$PO_4$[8] | 71.8 | 12.5 | 10.2 | 5.6 | 28.2 |
| $AlCl_3$ + $NiSO_4$ + $Al_2O_3$ | 89.6 | 8.7 | 1.1 | 0.7 | 10.4 |
| $AlCl_3$ + $NiSO_4$ + $SiO_2$ | 82.4 | 9.0 | 5.2 | 3.5 | 17.6 |
| $AlCl_3$ + $NiSO_4$ + $SiO_2/Al_2O_3$[1] | 76.8 | 15.9 | 3.8 | 3.6 | 23.2 |
| $AlCl_3$ + $NiSO_4$ + $SiO_2/Al_2O_3$[2] | 90.9 | 6.3 | 1.8 | 1.0 | 9.1 |
| $AlCl_3$ + $NiSO_4$ + Al—$PO_4$[6] | 86.9* | 12.3* | 0.4* | 0.5* | 13.1* |
| $AlCl_3$ + $CoSO_4$ + $Al_2O_3$ | 91.5 | 4.5 | 2.7 | 1.4 | 8.5 |
| $AlCl_3$ + $CoSO_4$ + $SiO_2$ | 82.6 | 8.7 | 4.9 | 3.8 | 17.4 |
| $AlCl_3$ + $CoSO_4$ + $SiO_2/Al_2O_3$[1] | 81.7 | 12.6 | 3.1 | 2.5 | 18.3 |
| $AlCl_3$ + $CoSO_4$ + $SiO_2/Al_2O_3$[2] | 81.3 | 11.9 | 3.6 | 3.3 | 18.7 |
| $AlCl_3$ + $CoSO_4$ + Al—$PO_4$[6] | 73.9 | 24.3 | 0.9 | 1.0 | 26.1 |
| $AlCl_3$ + $FeSO_4$ + $Al_2O_3$ | 91.0* | 7.3* | 0.9* | 0.8* | 9.0* |
| $AlCl_3$ + $FeSO_4$ + $SiO_2$ | 83.2 | 8.9 | 4.3 | 3.6 | 16.8 |

TABLE VI-continued

| Catalyst Preparation Method | Liquid Product Composition (Weight-%) | | | | % Conversion of n-Hexane |
|---|---|---|---|---|---|
| | n-Hexane | Isohexanes[9] | $C_4/C_5$ Alkanes | $C_7^+$ Alkanes | |
| $AlCl_3$ + $FeSO_4$ + $SiO_2/Al_2O_3$[1] | 72.2 | 16.9 | 5.7 | 5.2 | 27.8 |
| $AlCl_3$ + $FeSO_4$ + $SiO_2/Al_2O_3$[2] | 80.1 | 18.4 | 1.1 | 0.5 | 19.9 |
| $AlCl_3$ + $FeSO_4$ + $Al-PO_4$[6] | 91.0 | 8.7 | 0.1 | 0.3 | 9.0 |
| $AlCl_3$ + $MnSO_4$ + $Al_2O_3$ | 82.4 | 13.3 | 2.3 | 2.1 | 17.6 |
| $AlCl_3$ + $MnSO_4$ + $SiO_2$ | 77.5 | 13.9 | 4.4 | 4.2 | 22.5 |
| $AlCl_3$ + $MnSO_4$ + $SiO_2/Al_2O_3$[1] | 83.0* | 16.2* | 0.3* | 0.5* | 17.0* |
| $AlCl_3$ + $MnSO_4$ + $SiO_2/Al_2O_3$[2] | 79.5 | 12.6 | 4.2 | 3.8 | 20.5 |
| $AlCl_3$ + $MnSO_4$ + $Al-PO_4$[6] | 79.7* | 19.6* | 0.3* | 0.4* | 20.3* |
| $AlCl_3$ + $ZnSO_4$ + $Al_2O_3$ | 86.7* | 9.4* | 1.9* | 1.9* | 13.3* |
| $AlCl_3$ + $ZnSO_4$ + $SiO_2$ | 81.9 | 7.7 | 5.4 | 5.1 | 18.1 |
| $AlCl_3$ + $ZnSO_4$ + $SiO_2/Al_2O_3$[1] | 82.2 | 12.7 | 3.8 | 1.2 | 17.8 |
| $AlCl_3$ + $ZnSO_4$ + $SiO_2/Al_2O_3$[2] | 85.4 | 10.8 | 2.7 | 1.2 | 14.6 |
| $AlCl_3$ + $ZnSO_4$ + $Al-PO_4$[6] | 88.3* | 9.9* | 1.0* | 0.8* | 11.7* |
| $AlCl_3$ + $MgSO_4$ + $Al_2O_3$ | 86.7* | 9.8* | 2.8* | 0.8* | 12.3* |
| $AlCl_3$ + $MgSO_4$ + $SiO_2$ | 84.7 | 7.9 | 4.6 | 2.9 | 15.3 |
| $AlCl_3$ + $MgSO_4$ + $SiO_2/Al_2O_3$[1] | 71.7 | 17.0 | 5.4 | 5.8 | 28.3 |
| $AlCl_3$ + $MgSO_4$ + $SiO_2/Al_2O_3$[2] | 81.5 | 12.7 | 3.4 | 2.4 | 18.5 |
| $AlCl_3$ + $MgSO_4$ + $Al-PO_4$[6] | 73.9* | 17.7* | 4.8* | 3.7* | 26.1* |
| $AlCl_3$ + $CaSO_4$ + $Al_2O_3$ | 87.3 | 12.2 | 0.2 | 0.4 | 12.7 |
| $AlCl_3$ + $CaSO_4$ + $SiO_2$ | 95.0 | 3.2 | 1.0 | 0.8 | 5.0 |
| $AlCl_3$ + $CaSO_4$ + $SiO_2/Al_2O_3$[1] | 98.9* | 0.9* | 0* | 0.3* | 1.1* |
| $AlCl_3$ + $CaSO_4$ + $SiO_2/Al_2O_3$[2] | 87.1 | 9.8 | 2.2 | 1.0 | 12.9 |
| $AlCl_3$ + $CaSO_4$ + $Al-PO_4$[6] | 98.8* | 5.8* | 0* | 0.4* | 6.2* |

[1]50 weight-% silica + 50 weight-% $Al_2O_3$
[2]25 weight-% silica + 75 weight-% $AlO_3$
[3]aluminum phosphate/oxide having a P:Al atomic ratio of 0.2:1
[4]aluminum phosphate/oxide having a P:Al atomic ratio of 0.3:1
[5]aluminum phosphate/oxide having a P:Al atomic ratio of 0.4:1
[6]aluminum phosphate/oxide having a P:Al atomic ratio of 0.5:1
[7]aluminum phosphate/oxide having a P:Al atomic ratio of 0.6:1
[8]aluminum phosphate/oxide having a P:Al atomic ratio of 0.9:1
[9]primarily methylpentanes, some dimethylbutane
*data obtained after a reaction time of 2 hours Test results in Table VI indicate that generally the catalysts prepared from $AlCl_3$, $CuSO_4$ and either an aluminum phosphate/oxide having a P:Al atomic ratios of about 0.3-0.9:1 or a silica-alumina exhibited the highest activity.

EXAMPLE VIII

This example illustrates the use of the catalyst materials described in Example V for disproportionation/isomerization of isooctane (2,2,4-trimethylpentane), essentially in accordance with the procedure described in Example I, except that generally the reaction temperature was about 30°-40° C. Test results obtained after a reaction time of about 1 hour (in some cases after about 2 hours) are summarized in Table VII.

TABLE VII

| Catalyst Preparation Method | Liquid Product Composition (Weight-%) | | | | % Conversion of Isooctane |
|---|---|---|---|---|---|
| | n-Isooctane | Other $C_8$ Alkanes | $C_4$-$C_7$ Alkanes | $C_9^+$ Alkanes | |
| $AlCl_3$ + $CuSO_4$ + $Al_2O_3$ | 88.2 | 2.6 | 5.7 | 3.6 | 11.9 |
| $AlCl_3$ + $CuSO_4$ + $Al_2O_3$ | 87.9 | 2.3 | 7.7 | 2.1 | 12.1 |
| $AlCl_3$ + $CuSO_4$ + $SiO_2/Al_2O_3$[1] | 88.2 | 2.3 | 5.9 | 3.7 | 11.8 |
| $AlCl_3$ + $CuSO_4$ + $SiO_2/Al_2O_3$[2] | 85.5 | 2.9 | 6.6 | 5.1 | 14.5 |
| $AlCl_3$ + $CuSO_4$ + $SiO_2/Al_2O_3$[2] | 90.0 | 2.0 | 5.6 | 2.3 | 10.0 |
| $AlCl_3$ + $CuSO_4$ + $SiO_2/Al_2O_3$[2] | 88.0 | 2.3 | 7.2 | 2.5 | 12.0 |
| $AlCl_3$ + $CuSO_4$ + $Al-PO_4$[3] | 81.2 | 3.5 | 9.4 | 5.9 | 18.8 |
| $AlCl_3$ + $CuSO_4$ + $Al-PO_4$[4] | 83.6 | 2.9 | 8.1 | 5.4 | 16.4 |
| $AlCl_3$ + $CuSO_4$ + $Al-PO_4$[5] | 87.4 | 2.4 | 6.6 | 3.7 | 12.6 |
| $AlCl_3$ + $CuSO_4$ + $Al-PO_4$[5] | 83.3 | 2.9 | 8.2 | 5.6 | 16.7 |
| $AlCl_3$ + $CuSO_4$ + $Al-PO_4$[6] | 82.4 | 3.0 | 8.4 | 6.3 | 17.6 |
| $AlCl_3$ + $CuSO_3$ + $Al-PO_4$[7] | 84.2 | 2.7 | 8.2 | 5.0 | 15.8 |
| $AlCl_3$ + $NiSO_4$ + $Al_2O_3$ | 94.7 | 1.2 | 2.9 | 1.3 | 5.3 |
| $AlCl_3$ + $NiSO_4$ + $SiO_2/Al_2O_3$[1] | 94.2 | 1.6 | 2.9 | 1.2 | 5.8 |
| $AlCl_3$ + $CoSO_4$ + $Al_2O_3$ | 96.4 | 1.2 | 1.7 | 0.7 | 3.6 |
| $AlCl_3$ + $CoSO_4$ + $SiO_2/Al_2O_3$[2] | 94.2 | 1.5 | 2.9 | 1.3 | 5.8 |
| $AlCl_3$ + $FeSO_4$ + $Al_2O_3$ | 86.7 | 4.8 | 5.5 | 2.9 | 13.3 |
| $AlCl_3$ + $FeSO_4$ + $SiO_2/Al_2O_3$[2] | 92.7 | 1.8 | 3.7 | 1.9 | 7.3 |
| $AlCl_3$ + $MnSO_4$ + $Al_2O_3$ | 93.1 | 1.8 | 3.5 | 1.6 | 6.9 |
| $AlCl_3$ + $MnSO_4$ + $SiO_2/Al_2O_3$ | 93.6 | 1.8 | 3.1 | 1.6 | 6.4 |
| $AlCl_3$ + $ZnSO_4$ + $Al_2O_3$ | 94.3 | 1.5 | 3.2 | 1.0 | 5.7 |
| $AlCl_3$ + $ZnSO_4$ + $SiO_2/Al_2O_3$[2] | 93.9 | 1.6 | 3.5 | 0.9 | 6.1 |
| $AlCl_3$ + $MgSO_4$ + $Al_2O_3$ | 92.3 | 1.9 | 4.0 | 1.8 | 7.7 |
| $AlCl_3$ + $MgSO_4$ + $SiO_2/Al_2O_3$[2] | 92.7 | 1.8 | 3.6 | 1.8 | 7.3 |
| $AlCl_3$ + $CaSO_4$ + $Al_2O_3$ | 93.7 | 1.4 | 4.0 | 1.0 | 6.3 |

TABLE VII-continued

| Catalyst Preparation Method | Liquid Product Composition (Weight-%) | | | | % Conversion of Isooctane |
|---|---|---|---|---|---|
| | n-Isooctane | Other $C_8$ Alkanes | $C_4$-$C_7$ Alkanes | $C_9^+$ Alkanes | |
| $AlCl_3$ + $CaSO_4$ + $SiO_2/Al_2O_3^2$ | 95.0 | 1.0 | 2.8 | 1.2 | 5.0 |

[1] 50 weight-% silica + 50 weight-% $Al_2O_3$
[2] 25 weight-% silica + 75 weight-% $AlO_3$
[3] aluminum phosphate/oxide having a P:Al atomic ratio of 0.2:1
[4] aluminum phosphate/oxide having a P:Al atomic ratio of 0.3:1
[5] aluminum phosphate/oxide having a P:Al atomic ratio of 0.4:1
[6] aluminum phosphate/oxide having a P:Al atomic ratio of 0.6:1
[7] aluminum phosphate/oxide having a P:Al atomic ratio of 0.9:1
*data obtained after a reaction time of 2 hours Test results in Table VII indicate that the catalysts prepared from $AlCl_3$, $CuSO_4$ and either an aluminum phosphate/oxide or a silica-alumina were most active.

EXAMPLE IX

This example illustrates the use of the catalyst materials described in Example V for isopentane (2-methylbutane) disproportionation/isomerization, essentially in accordance with the procedure described in Example I, except that generally the reaction temperature was about 30°–40° C. Test results obtained after a reaction time of about 1 hour (in some cases after about 2 hours) are summarized in Table VIII.

TABLE VIII

| Catalyst Preparation Method | Liquid Product Composition (Weight-%) | | | | % Conversion of Isopentane |
|---|---|---|---|---|---|
| | Isopentane | n-Pentane | Isobutane | $C_6^+$ Alkanes | |
| $AlCl_3$ + $CuSO_4$ + $Al_2O_3$ | 55.6 | 4.7 | 1.7 | 38.1 | 44.4 |
| $AlCl_3$ + $CuSO_4$ + $Al_2O_3$ | 49.8 | 4.5 | 12.0 | 33.6 | 50.2 |
| $AlCl_3$ + $CuSO_4$ + $SiO_2$ | 33.9 | 5.2 | 30.2 | 30.7 | 66.1 |
| $AlCl_3$ + $CuSO_4$ + $SiO_2/Al_2O_3^1$ | 57.3 | 7.7 | 10.1 | 25.0 | 42.7 |
| $AlCl_3$ + $CuSO_4$ + $SiO_2/Al_2O_3^2$ | 31.1 | 8.4 | 6.5 | 53.9 | 68.9 |
| $AlCl_3$ + $CuSO_4$ + $SiO_2/Al_2O_3^2$ | 31.5 | 7.3 | 25.4 | 35.9 | 68.5 |
| $AlCl_3$ + $CuSO_4$ + Al—$PO_4^3$ | 87.2 | 3.6 | 4.0 | 5.1 | 12.8 |
| $AlCl_3$ + $CuSO_4$ + Al—$PO_4^4$ | 36.3 | 9.3 | 21.3 | 33.2 | 63.7 |
| $AlCl_3$ + $CuSO_4$ + Al—$PO_4^5$ | 34.8 | 7.7 | 18.8 | 38.7 | 65.2 |
| $AlCl_3$ + $CuSO_4$ + Al—$PO_4^5$ | 51.3 | 8.6 | 17.4 | 22.7 | 48.7 |
| $AlCl_3$ + $CuSO_4$ + Al—$PO_4^6$ | 58.1 | 7.7 | 16.1 | 18.1 | 41.9 |
| $AlCl_3$ + $CuSO_4$ + Al—$PO_4^7$ | 51.5 | 7.8 | 21.2 | 19.5 | 48.5 |
| $AlCl_3$ + $CuSO_3$ + Al—$PO_4^8$ | 72.9 | 7.7 | 3.9 | 15.6 | 27.1 |
| $AlCl_3$ + $NiSO_4$ + $Al_2O_3$ | 91.8* | 2.8* | 1.8* | 3.6* | 8.2* |
| $AlCl_3$ + $NiSO_4$ + $SiO_2$ | 50.1 | 4.7 | 10.3 | 34.9 | 49.1 |
| $AlCl_3$ + $NiSO_4$ + $SiO_2/Al_2O_3^1$ | 78.6 | 6.4 | 1.1 | 13.9 | 21.4 |
| $AlCl_3$ + $NiSO_4$ + $SiO_2/Al_2O_3^2$ | 44.3 | 5.8 | 10.3 | 39.6 | 55.7 |
| $AlCl_3$ + $NiSO_4$ + Al—$PO_4^6$ | 72.0 | 6.0 | 6.1 | 15.9 | 28.0 |
| $AlCl_3$ + $CoSO_4$ + $Al_2O_3$ | 45.8* | 8.8* | 5.5* | 39.9* | 54.2 |
| $AlCl_3$ + $CoSO_4$ + $SiO_2$ | 32.2 | 4.7 | 32.1 | 31.0 | 67.8 |
| $AlCl_3$ + $CoSO_4$ + $SiO_2/Al_2O_3^1$ | 59.4 | 5.5 | 6.4 | 28.5 | 40.6 |
| $AlCl_3$ + $CoSO_4$ + $SiO_2/Al_2O_3^2$ | 65.3 | 6.2 | 11.8 | 16.7 | 34.7 |
| $AlCl_3$ + $CoSO_4$ + Al—$PO_4^6$ | 78.7 | 5.6 | 5.5 | 10.3 | 21.3 |
| $AlCl_3$ + $FeSO_4$ + $Al_2O_3$ | 75.9* | 4.7* | 5.8* | 13.6* | 24.1* |
| $AlCl_3$ + $FeSO_4$ + $SiO_2$ | 30.6 | 5.0 | 34.1 | 30.3 | 69.4 |
| $AlCl_3$ + $FeSO_4$ + $SiO_2/Al_2O_3^1$ | 63.6 | 4.6 | 7.9 | 23.9 | 36.4 |
| $AlCl_3$ + $FeSO_4$ + $SiO_2/Al_2O_3^2$ | 72.5 | 6.4 | 6.8 | 14.3 | 27.5 |
| $AlCl_3$ + $FeSO_4$ + Al—$PO_4^6$ | 75.8* | 7.6* | 2.1* | 14.4* | 24.2* |
| $AlCl_3$ + $MnSO_4$ + $Al_2O_3$ | 82.8* | 7.0* | 3.8* | 6.4* | 17.2* |
| $AlCl_3$ + $MnSO_4$ + $SiO_2$ | 73.9 | 4.3 | 5.4 | 16.4 | 26.1 |
| $AlCl_3$ + $MnSO_4$ + $SiO_2/Al_2O_3^1$ | 87.2 | 4.6 | 0.5 | 7.8 | 12.9 |
| $AlCl_3$ + $MnSO_4$ + $SiO_2/Al_2O_3^2$ | 48.1 | 5.5 | 2.4 | 44.0 | 51.9 |
| $AlCl_3$ + $MnSO_4$ + Al—$PO_4^6$ | 82.8 | 5.9 | 2.6 | 8.7 | 17.2 |
| $AlCl_3$ + $ZnSO_4$ + $Al_2O_3$ | 89.1* | 5.5* | 2.2* | 3.3* | 10.9* |
| $AlCl_3$ + $ZnSO_4$ + $SiO_2$ | 25.7 | 5.4 | 33.7 | 35.2 | 74.3 |
| $AlCl_3$ + $ZnSO_4$ + $SiO_2/Al_2O_3^1$ | 88.1 | 4.6 | 1.8 | 5.4 | 11.9 |
| $AlCl_3$ + $ZnSO_4$ + $SiO_2/Al_2O_3^2$ | 81.2 | 3.5 | 6.9 | 8.5 | 18.8 |
| $AlCl_3$ + $ZnSO_4$ + Al—$PO_4^6$ | 90.4 | 4.5 | 1.4 | 3.8 | 9.6 |
| $AlCl_3$ + $MgSO_4$ + $Al_2O_3$ | 84.3* | 6.1* | 3.2* | 6.4* | 15.7* |
| $AlCl_3$ + $MgSO_4$ + $SiO_2$ | 36.7 | 4.6 | 28.4 | 30.4 | 63.3 |
| $AlCl_3$ + $MgSO_4$ + $SiO_2/Al_2O_3^1$ | 67.8* | 7.6* | 3.4* | 21.2* | 32.2* |
| $AlCl_3$ + $MgSO_4$ + $SiO_2/Al_2O_3^2$ | 83.9 | 4.2 | 3.7 | 8.2 | 16.1 |
| $AlCl_3$ + $MgSO_4$ + Al—$PO_4^6$ | 89.8 | 4.1 | 1.7 | 4.4 | 10.2 |
| $AlCl_3$ + $CaSO_4$ + $Al_2O_3$ | 78.4* | 6.4* | 4.2* | 11.0* | 21.6* |
| $AlCl_3$ + $CaSO_4$ + $SiO_2$ | 48.1 | 3.9 | 23.4 | 24.6 | 51.9 |
| $AlCl_3$ + $CaSO_4$ + $SiO_2/Al_2O_3^1$ | 95.5 | 1.5 | 0.5 | 2.5 | 4.5 |
| $AlCl_3$ + $CaSO_4$ + $SiO_2/Al_2O_3^2$ | 82.1 | 3.9 | 5.8 | 8.2 | 17.9 |

TABLE VIII-continued

| Catalyst Preparation Method | Liquid Product Composition (Weight-%) | | | | % Conversion of Isopentane |
|---|---|---|---|---|---|
| | Isopentane | n-Pentane | Isobutane | $C_6^+$ Alkanes | |
| $AlCl_3$ + $CaSO_4$ + Al—$PO_4$[6] | 74.5* | 7.7* | 5.2* | 12.6 | 25.5* |

[1] 50 weight-% silica + 50 weight-% $Al_2O_3$
[2] 25 weight-% silica + 75 weight-% $AlO_3$
[3] aluminum phosphate/oxide having a P:Al atomic ratio of 0.2:1
[4] aluminum phosphate/oxide having a P:Al atomic ratio of 0.3:1
[5] aluminum phosphate/oxide having a P:Al atomic ratio of 0.4:1
[6] aluminum phosphate/oxide having a P:Al atomic ratio of 0.5:1
[7] aluminum phosphate/oxide having a P:Al atomic ratio of 0.6:1
[8] aluminum phosphate/oxide having a P:Al atomic ratio of 0.9:1
*data obtained after a reaction time of 2 hours Test results in Table VIII indicate that generally the catalysts prepared from $AlCl_3$ and $CuSO_4$ were most active, regardless of the employed inorganic support materials. Of the remaining catalysts, generally silica and silica-aluminas were the most effective support materials.

EXAMPLE X

This example illustrates the use of some of the catalyst materials described in Example v for the disproportionation/isomerization of a commercial alkylate (obtained from a refinery of Phillips Petroleum Company), essentially in accordance with the procedure described in Example I, except that generally the reaction temperature was about 30°–40° C. The feed volume was 10 mL, and the catalyst weight was 0.5 gram. Test results obtained after a reaction time of about 1 hour are summarized in Table IX.

TABLE IX

| Catalyst Preparation Method | Liquid Product Composition (Weight-%) | | | Octane Number[9] | Reid Vapor Pressure[10] |
|---|---|---|---|---|---|
| | $C_4$–$C_7$ Alkanes | $C_8$ Alkanes | $C_9^+$ Alkanes | | |
| - (Feed) | 29.4 | 63.6 | 7.0 | 91.4 | 3.1 |
| $AlCl_3$ + $CuSO_4$ + $Al_2O_3$ | 34.1 | 50.0 | 15.9 | 91.2 | 11.9 |
| $AlCl_3$ + $CuSO_4$ + $Al_2O_3$ | 32.5 | 53.1 | 14.4 | 91.4 | 10.9 |
| $AlCl_3$ + $CuSO_4$ + $Al_2O_3$ | 34.0 | 50.9 | 15.0 | 91.7 | 11.8 |
| $AlCl_3$ + $CuSO_4$ + $Al_2O_3$ | 31.6 | 58.4 | 11.1 | 91.4 | 6.6 |
| $AlCl_3$ + $CuSO_4$ + $SiO_2$ | 33.5 | 50.9 | 15.5 | 91.6 | 12.4 |
| $AlCl_3$ + $CuSO_4$ + $SiO_2/Al_2O_3$[1] | 33.5 | 48.4 | 18.1 | 91.2 | 12.4 |
| $AlCl_3$ + $CuSO_4$ + $SiO_2/Al_2O_3$[2] | 34.2 | 46.9 | 18.9 | 91.2 | 13.7 |
| $AlCl_3$ + $CuSO_4$ + $SiO_2/Al_2O_3$[2] | 37.3 | 48.1 | 14.6 | 91.2 | 14.1 |
| $AlCl_3$ + $CuSO_4$ + Al—$PO_4$[3] | 35.8 | 52.3 | 11.9 | 91.2 | 11.4 |
| $AlCl_3$ + $CuSO_4$ + Al—$PO_4$[4] | 38.7 | 48.2 | 13.1 | 92.0 | 15.3 |
| $AlCl_3$ + $CuSO_4$ + Al—$PO_4$[5] | 34.4 | 48.1 | 17.3 | 91.5 | 13.4 |
| $AlCl_3$ + $CuSO_4$ + Al—$PO_4$[5] | 36.4 | 48.1 | 15.5 | 91.5 | 14.6 |
| $AlCl_3$ + $CuSO_4$ + Al—$PO_4$[6] | 32.4 | 46.4 | 21.2 | 90.6 | 9.8 |
| $AlCl_3$ + $CuSO_4$ + Al—$PO_4$[7] | 38.4 | 47.4 | 14.2 | 90.9 | 14.1 |
| $AlCl_3$ + $CuSO_4$ + Al—$PO_4$[8] | 37.6 | 47.2 | 15.2 | 88.4 | 12.9 |
| $AlCl_3$ + $NiSO_4$ + $SiO_2$ | 33.4 | 56.2 | 10.4 | 92.0 | 9.1 |
| $AlCl_3$ + $NiSO_4$ + $SiO_2/Al_2O_3$[1] | 31.5 | 58.4 | 10.2 | 86.6 | 6.8 |
| $AlCl_3$ + $NiSO_4$ + Al—$PO_4$[6] | 30.5 | 58.8 | 10.7 | 91.8 | 6.8 |
| $AlCl_3$ + $CoSO_4$ + $SiO_2$ | 34.0 | 52.7 | 13.4 | 91.6 | 10.9 |
| $AlCl_3$ + $CoSO_4$ + $SiO_2/Al_2O_3$[1] | 33.4 | 54.4 | 12.2 | 91.9 | 9.9 |
| $AlCl_3$ + $CoSO_4$ + Al—$PO_4$[6] | 31.3 | 57.8 | 10.9 | 91.7 | 7.4 |
| $AlCl_3$ + $FeSO_4$ + $SiO_2$ | 34.1 | 51.3 | 14.6 | 91.8 | 11.6 |
| $AlCl_3$ + $FeSO_4$ + $SiO_2/Al_2O_3$[1] | 33.0 | 55.2 | 11.7 | 91.9 | 9.4 |
| $AlCl_3$ + $FeSO_4$ + Al—$PO_4$[6] | 30.4 | 54.4 | 15.2 | 90.6 | 8.3 |
| $AlCl_3$ + $MnSO_4$ + $SiO_2$ | 31.5 | 59.5 | 9.1 | 91.8 | 6.0 |
| $AlCl_3$ + $MnSO_4$ + $SiO_2/Al_2O_3$[1] | 31.8 | 55.5 | 12.7 | 86.7 | 7.8 |
| $AlCl_3$ + $MnSO_4$ + Al—$PO_4$[6] | 30.8 | 58.9 | 10.3 | 92.2 | 6.9 |
| $AlCl_3$ + $ZnSO_4$ + $SiO_2$ | 32.0 | 55.7 | 12.2 | 91.8 | 8.5 |
| $AlCl_3$ + $ZnSO_4$ + $SiO_2/Al_2O_3$ | 31.1 | 59.7 | 9.3 | 91.8 | 6.0 |
| $AlCl_3$ + $ZnSO_4$ + Al—$PO_4$[6] | 34.1 | 57.8 | 8.1 | 91.2 | 7.9 |
| $AlCl_3$ + $MgSO_4$ + $SiO_2$ | 33.3 | 53.7 | 13.0 | 91.8 | 9.9 |
| $AlCl_3$ + $MgSO_4$ + $SiO_2/Al_2O_3$[1] | 35.3 | 57.0 | 7.7 | 91.8 | 7.4 |
| $AlCl_3$ + $MgSO_4$ + Al—$PO_4$[6] | 33.9 | 54.9 | 11.1 | 91.6 | 10.2 |
| $AlCl_3$ + $CaSO_4$ + $SiO_2$ | 35.5 | 55.5 | 9.1 | 89.6 | 8.5 |
| $AlCl_3$ + $CaSO_4$ + $SiO_2/Al_2O_3$[1] | 32.2 | 55.9 | 11.8 | 91.6 | 9.2 |
| $AlCl_3$ + $CaSO_4$ + Al—$PO_4$[6] | 31.8 | 57.0 | 11.2 | 92.1 | 8.8 |

[1] 50 weight-% silica + 50 weight-% $Al_2O_3$
[2] 25 weight-% silica + 75 weight-% $AlO_3$
[3] aluminum phosphate/oxide having a P:Al atomic ratio of 0.2:1
[4] aluminum phosphate/oxide having a P:Al atomic ratio of 0.3:1
[5] aluminum phosphate/oxide having a P:Al atomic ratio of 0.4:1
[6] aluminum phosphate/oxide having a P:Al atomic ratio of 0.5:1
[7] aluminum phosphate/oxide having a P:Al atomic ratio of 0.6:1
[8] aluminum phosphate/oxide having a P:Al atomic ratio of 0.9:1
[9] (research octane number + motor octane number) divided by 2
[10] in psi units, measured at 100° F.

Test data in Table IX indicate that generally the product had a greater vapor pressure than the feed alkylate, whereas the octane number of products and feeds were generally comparable. Thus, the isomerization/disproportionation process of this invention can be utilized to adjust the vapor pressure of fuel feedstocks.

EXAMPLE XI

This example illustrates the use of the catalyst materials described in Example V for the isomerization of methylcyclopentane to cyclohexane, essentially in accordance with the procedure described in Example I, except that generally the reaction temperature was about 30°-40° C. Test results obtained after a reaction time of about 1 hour (in some cases after about 2 hours) are summarized in Table X.

TABLE X

| Catalyst Preparation Method | Liquid Product Composition (Weight-%) | | % Conversion of Methylcyclopentane |
|---|---|---|---|
| | Methylcyclopentane | Cyclohexane | |
| $AlCl_3 + CuSO_4 + Al_2O_3$ | 62.1 | 37.2 | 37.9 |
| $AlCl_3 + CuSO_4 + Al_2O_3$ | 24.5 | 73.3 | 75.5 |
| $AlCl_3 + CuSO_4 + SiO_2$ | 25.0 | 71.0 | 75.0 |
| $AlCl_3 + CuSO_4 + SiO_2/Al_2O_3^1$ | 63.5 | 35.0 | 36.5 |
| $AlCl_3 + CuSO_4 + SiO_2/Al_2O_3^2$ | 70.8 | 27.6 | 29.2 |
| $AlCl_3 + CuSO_4 + SiO_2/Al_2O_3^2$ | 59.8 | 40.2 | 40.2 |
| $AlCl_3 + CuSO_4 + SiO_2/Al_2O_3^2$ | 23.0 | 74.4 | 77.0 |
| $AlCl_3 + CuSO_4 + Al-PO_4^3$ | 38.8 | 58.8 | 61.2 |
| $AlCl_3 + CuSO_4 + Al-PO_4^4$ | 36.7 | 61.2 | 63.3 |
| $AlCl_3 + CuSO_4 + Al-PO_4^5$ | 25.4 | 70.6 | 74.6 |
| $AlCl_3 + CuSO_4 + Al-PO_4^5$ | 26.1 | 72.2 | 73.4 |
| $AlCl_3 + CuSO_4 + Al-PO_4^6$ | 48.9 | 50.2 | 51.1 |
| $AlCl_3 + CuSO_4 + Al-PO_4^7$ | 29.4 | 68.9 | 70.6 |
| $AlCl_3 + CuSO_3 + Al-PO_4^8$ | 34.2 | 64.1 | 65.0 |
| $AlCl_3 + NiSO_4 + Al_2O_3$ | 82.6* | 13.8* | 17.4* |
| $AlCl_3 + NiSO_4 + SiO_2$ | 80.5 | 17.5 | 19.5 |
| $AlCl_3 + NiSO_4 + SiO_2/Al_2O_3^1$ | 83.9 | 15.8 | 16.1 |
| $AlCl_3 + NiSO_4 + SiO_2/Al_2O_3^2$ | 78.5 | 20.9 | 21.5 |
| $AlCl_3 + NiSO_4 + Al-PO_4^6$ | 83.5 | 15.4 | 16.5 |
| $AlCl_3 + CoSO_4 + Al_2O_3$ | 69.1 | 30.2 | 30.9 |
| $AlCl_3 + CoSO_4 + SiO_2$ | 62.3 | 35.5 | 37.7 |
| $AlCl_3 + CoSO_4 + SiO_2/Al_2O_3^1$ | 90.6 | 9.1 | 9.4 |
| $AlCl_3 + CoSO_4 + SiO_2/Al_2O_3^2$ | 80.7 | 17.9 | 19.3 |
| $AlCl_3 + CoSO_4 + Al-PO_4^6$ | 76.2 | 23.0 | 23.8 |
| $AlCl_3 + FeSO_4 + Al_2O_3$ | 82.8 | 14.7 | 17.2 |
| $AlCl_3 + FeSO_4 + SiO_2$ | 70.6 | 27.2 | 29.4 |
| $AlCl_3 + FeSO_4 + SiO_2/Al_2O_3^1$ | 89.7 | 10.0 | 10.3 |
| $AlCl_3 + FeSO_4 + SiO_2/Al_2O_3^2$ | 69.6 | 29.9 | 30.4 |
| $AlCl_3 + FeSO_4 + Al-PO_4^6$ | 82.0 | 17.1 | 18.0 |
| $AlCl_3 + MnSO_4 + Al_2O_3$ | 83.7 | 14.1 | 16.3 |
| $AlCl_3 + MnSO_4 + SiO_2$ | 92.5 | 6.0 | 7.5 |
| $AlCl_3 + MnSO_4 + SiO_2/Al_2O_3^1$ | 91.6 | 8.1 | 8.4 |
| $AlCl_3 + MnSO_4 + SiO_2/Al_2O_3^2$ | 87.4 | 11.4 | 12.6 |
| $AlCl_3 + MnSO_4 + Al-PO_4^6$ | 80.1 | 19.1 | 19.9 |
| $AlCl_3 + ZnSO_4 + Al_2O_3$ | 88.3 | 11.0 | 11.7 |
| $AlCl_3 + ZnSO_4 + SiO_2$ | 76.1 | 21.2 | 27.9 |
| $AlCl_3 + ZnSO_4 + SiO_2/Al_2O_3^1$ | 84.7* | 14.4* | 15.3* |
| $AlCl_3 + ZnSO_4 + SiO_2/Al_2O_3^2$ | 88.6 | 8.3 | 11.4 |
| $AlCl_3 + ZnSO_4 + Al-PO_4^6$ | 88.8 | 10.4 | 11.2 |
| $AlCl_3 + MgSO_4 + Al_2O_3$ | 88.7 | 9.6 | 11.3 |
| $AlCl_3 + MgSO_4 + SiO_2$ | 30.6 | 65.6 | 69.4 |
| $AlCl_3 + MgSO_4 + SiO_2/Al_2O_3^1$ | 97.8 | 1.9 | 2.2 |
| $AlCl_3 + MgSO_4 + SiO_2/Al_2O_3^2$ | 88.7 | 10.4 | 11.3 |
| $AlCl_3 + MgSO_4 + Al-PO_4^6$ | 87.1 | 12.2 | 12.9 |
| $AlCl_3 + CaSO_4 + Al_2O_3$ | 81.1 | 16.0 | 18.9 |
| $AlCl_3 + CaSO_4 + SiO_2$ | 96.0 | 2.2 | 4.0 |
| $AlCl_3 + CaSO_4 + SiO_2/Al_2O_3^1$ | 98.7 | 1.0 | 1.3 |
| $AlCl_3 + CaSO_4 + SiO_2/Al_2O_3^2$ | 95.2 | 4.1 | 4.8 |
| $AlCl_3 + CaSO_4 + Al-PO_4^6$ | 92.1 | 7.2 | 7.9 |

[1] 50 weight-% silica + 50 weight-% $Al_2O_3$
[2] 25 weight-% silica + 75 weight-% $Al_2O_3$
[3] aluminum phosphate/oxide having a P:Al atomic ratio of 0.2:1
[4] aluminum phosphate/oxide having a P:Al atomic ratio of 0.3:1
[5] aluminum phosphate/oxide having a P:Al atomic ratio of 0.4:1
[6] aluminum phosphate/oxide having a P:Al atomic ratio of 0.5:1
[7] aluminum phosphate/oxide having a P:Al atomic ratio of 0.6:1
[8] aluminum phosphate/oxide having a P:Al atomic ratio of 0.9:1
*data obtained after a reaction time of 2 hours Test results in Table X indicate that the catalysts prepared from $AlCl_3$, $CuSO_4$ and any of the employed solid inorganic support materials were most active as catalysts for the isomerization of methylcyclopentane. Test data in Table X also indicate that essentially all converted methylcyclopentane was isomerized to cyclohexane, with little or no disproportionation (to higher and lower hydrocarbons) occurring.

EXAMPLE XII

This example illustrates the use of sulfuric acid-pretreated support materials in the preparation of the catalyst compositions of this invention. 23 grams of several support materials (described earlier) were treated with 100 mL of 0.1 normal aqueous sulfuric acid for about 20 minutes, filtered, dried under vacuum conditions (0.1 mm Hg) for about 2 hours, and calcined at 600° C. for 2 hours in a nitrogen atmosphere. The support materials that had been $H_2SO_4$-pretreated, as described above, were alumina (described in Example II), silica (described in Example V) and two silica-aluminas (described in Example V).

A mixture of 1.78–3.56 grams (13.3–26.6 millimoles) of AlCl$_3$, 0.4–0.8 grams (2.5–5.0 millimoles) of CuSO$_4$, 5.0 grams of one of the H$_2$SO$_4$-pretreated support materials, and 65 mL of dry CCl$_4$ was heated for 18 hours under reflux conditions in the dark under a nitrogen atmosphere. The reaction slurry was cooled and filtered, and the separated solid catalyst was dried under vacuum conditions (as described in Example II).

The thus-prepared catalysts were employed in the isomerization/disproportionation of several alkanes (n-pentane, n-hexane, isopentane) essentially in accordance with the procedures of Examples VI, VII and IX, and in the isomerization of methylcyclopentane to cyclohexane in accordance with the procedure of Example XI. Preliminary test results (not presented in detail herein) indicate that frequently (but not always) the catalyst materials which had been prepared employing H$_2$SO$_4$-pretreated support materials were more active hydrocarbon conversion catalysts than the corresponding catalyst materials prepared with support materials which had not been pretreated with H$_2$SO$_4$.

Reasonable variations, modifications and adaptations for various conditions and reactants can be made within the scope of the disclosure and the appended claims without departing from the scope of this invention.

That which is claimed is:

1. A cycloalkane conversion process which comprises contacting, at a temperature of up to about 100° C., at least one cycloalkane containing 5–10 carbon atoms per molecule with an isomerization catalyst composition, at such contacting conditions as to at least partially convert said at least one feed cycloalkane to at least one product cycloalkane isomer, wherein said isomerization catalyst composition has been prepared by a preparation method consisting essentially of the steps of:
   (1) heating for a period of at least 1 hour, at a temperature in the range of about 40° C. to about 90° C., in the substantial absence of water: a mixture consisting essentially of (a) aluminum chloride (b) at least one metal salt selected from the group consisting of copper(II) sulfate, iron(II) sulfate, cobalt(II) sulfate, nickel(II) sulfate, manganese(II) sulfate, zinc sulfate, magnesium sulfate and calcium sulfate, (c) at least one solid inorganic refractory material having a surface area, measured by the BET method employing N$_2$, of at least 50 m$^2$/g, selected from the group consisting of alumina, silica, silica-alumina, aluminum phosphate and aluminum phosphate/oxide, and (d) at least one chlorinated hydrocarbon selected from the group consisting of dichloromethane, chloroform, carbon tetrachloride, 1,1-dichloroethane, 1,2-dichloroethane, 1,1,1-trichloroethane, 1,1-dichloropropane, 2,2-dichloropropane, 1-chlorobutane and 2-chloro-2-methylbutane; wherein the molar ratio of aluminum chloride to said at least one metal salt is at least about 2:1; and
   (2) separating the solid component of the reaction mixture formed in step (1) from said at least one chlorinated hydrocarbon under a dry gas atmosphere.

2. A process in accordance with claim 1 wherein said at least one chlorinated hydrocarbon is carbon tetrachloride.

3. A process in accordance with claim 1, wherein said at least one metal salt is CuSO$_4$.

4. A process in accordance with claim 1, wherein said molar ratio of aluminum chloride to said at least one metal salt is about 5:1 to about 6:1, said surface area of said at least one solid inorganic refractory material is about 100–400 m$^2$/g, step (1) is carried out in an inert gas atmosphere, and the heating time in step (1) is about 5–30 hours.

5. A process in accordance with claim 1, wherein step (2) is carried out under an inert gas atmosphere in two substeps: filtering the reaction mixture formed in step (1) so as to recover said solid component therefrom, and then drying the recovered solid material.

6. A process in accordance with claim 1, wherein the ratio of the combined weights of agents (a) and (b) to the weight of agent (c) is about 0.5:1 to about 5:1.

7. A process in accordance with claim 6, wherein the ratio of the weight of agent (d) to the combined weights of agents (a), (b) and (c) is about 4:1 to about 20:1.

8. A process in accordance with claim 1 wherein said contacting conditions for at least partially converting said at least one feed cycloalkane to said at least one product cycloalkane isomer comprise a reaction temperature of about 20°–50° C. and a reaction time of about 5 minutes to about 8 hours.

9. A process in accordance with claim 8, wherein said at least one feed cycloalkane is methylcyclopentane and said at least one product cycloalkane isomer is cyclohexane.

10. An alkane conversion process which comprises the step of contacting, at a temperature of up to about 100° C., at least one feed alkane containing 4–10 carbon atoms per molecule with an isomerization catalyst composition, at such contacting conditions as to convert said at least one feed alkane to at least one product alkane isomer, wherein said isomerization catalyst composition has been prepared by a preparation method consisting essentially of the steps of:
   (1) heating for a period of at least 1 hour, at a temperature in the range of about 40° C. to about 90° C., in the substantial absence of water: a mixture consisting essentially of (a) aluminum chloride, (b) at least one metal salt selected from the group consisting of copper(II) sulfate, iron(II) sulfate, cobalt(II) sulfate, nickel(II) sulfate, manganese(II) sulfate, zinc sulfate, magnesium sulfate and calcium sulfate, (c) at least one solid inorganic refractory material having a surface area, measured by the BET method employing N$_2$, of at least 50 m$^2$/g, selected from the group consisting of alumina, silica, silica-alumina, aluminum phosphate and aluminum phosphate/oxide, and (d) at least one chlorinated hydrocarbon selected from the group consisting of dichloromethane, chloroform, carbon tetrachloride, 1,1-dichloroethane, 1,2-dichloroethane, 1,1,1-trichloroethane, 1,1-dichloropropane, 2,2-dichloropropane, 1-chlorobutane and 2-chloro-2-methylbutane; wherein the molar ratio of aluminum chloride to said at least one metal salt is at least about 2:1; and
   (2) separating the solid component of the reaction mixture formed in step (1) from said at least one chlorinated hydrocarbon under a dry gas atmosphere.

11. A process in accordance with claim 10, therein said at least one chlorinated hydrocarbon is carbon tetrachloride.

12. A process in accordance with claim 10, wherein said at least one metal salt is CuSO$_4$.

13. A process in accordance with claim 10, wherein said molar ratio of aluminum chloride to said at least one metal salt is about 5:1 to about 6:1, said surface area of said at least one solid inorganic refractory material is about 100–400 m$^2$/g, step (1) is carried out under an inert gas atmosphere, and the heating time in step (1) is about 5–30 hours.

14. A process in accordance with claim 10, wherein step (2) is carried out under an inert gas atmosphere in two substeps: filtering the reaction mixture formed in step (1) so as to recover said solid component therefrom, and then drying the recovered solid material.

15. A process in accordance with claim 10, wherein the ratio of the combined weights of agents (a) and (b) to the weight of agent (c) is about 0.5:1 to about 5:1.

16. A process in accordance with claim 15, wherein the ratio of the weight of agent (d) to the combined weights of agents (a), (b) and (c) is about 4:1 to about 20:1.

17. A process in accordance with claim 10, wherein said contacting conditions for at least partially converting said at least one feed alkane to said at least one product alkane isomer comprise a reaction temperature of about 20°–50° C. and a reaction time of about 5 minutes to about 8 hours.

18. A process in accordance with claim 10, wherein said at least one feed alkane is selected from the group consisting of straight-chain alkanes containing 5–8 carbon atoms per molecule.

19. A process in accordance with claim 10, wherein said at least one feed alkane is selected from the group consisting of branched alkanes containing 5–8 carbon atoms per molecule.

20. A process in accordance with claim 10, wherein said at least one feed alkane is a product from an alkylation process.

21. A process in accordance with claim 1, wherein said solid inorganic refractory material is selected from the group consisting of Al$_2$O$_3$, SiO$_2$ and SiO$_2$—Al$_2$O$_3$ and has been pretreated with aqueous sulfuric acid.

22. A process in accordance with claim 10, wherein said solid inorganic refractory material is selected from the group consisting of Al$_2$O$_3$, SiO$_2$ and SiO$_2$—Al$_2$O$_3$ and has been pretreated with aqueous sulfuric acid.

23. A process in accordance with claim 1, wherein said at least one feed alkane is selected from the group consisting of n-pentane, 2-methylbutane, n-hexane and 2,2,4-trimethylpentane.

* * * * *

UNITED STATES PATENT AND TRADEMARK OFFICE
CERTIFICATE OF CORRECTION

PATENT NO. : 5,254,794

DATED : October 19, 1993

INVENTOR(S) : An-hsiang Wu

It is certified that error appears in the above-identified patent and that said Letters Patent is hereby corrected as shown below:

Claim 23, Column 22, line 22, delete "1" after "claim" and substitute --- 10 --- therefor.

Signed and Sealed this

First Day of March, 1994

Attest:

BRUCE LEHMAN

Attesting Officer

Commissioner of Patents and Trademarks